United States Patent [19]

Ciavatta

[11] 4,201,235

[45] May 6, 1980

[54] AMINO ACID-VITAMIN FORMULATIONS FOR SKIN, HAIR AND SCALP CONDITIONERS

[75] Inventor: Vitale G. Ciavatta, East Hanover, N.J.

[73] Assignee: Mare Corporation, Fairfield, N.J.

[21] Appl. No.: 866,348

[22] Filed: Jan. 3, 1978

[51] Int. Cl.² .................... A45D 19/16; A61K 7/06
[52] U.S. Cl. ................... 132/7; 424/DIG. 1; 424/47; 424/70; 424/237; 424/263; 424/266; 424/284; 424/319; 424/365
[58] Field of Search ............... 424/DIG. 4, 319, 284, 424/237, 263, 266, 365, 70, 47; 128/1 R; 132/7

[56] References Cited

U.S. PATENT DOCUMENTS

| | | | |
|---|---|---|---|
| 2,887,437 | 5/1959 | Klioze et al. | 424/319 X |
| 3,256,095 | 6/1966 | Crosby et al. | 424/319 X |
| 3,697,287 | 10/1972 | Winitz | 424/319 X |
| 3,773,930 | 11/1973 | Mohammed | 424/319 X |
| 3,778,502 | 12/1973 | Aubin et al. | 424/266 |

FOREIGN PATENT DOCUMENTS

| | | | |
|---|---|---|---|
| 1492121 | 3/1969 | Fed. Rep. of Germany | 424/319 |
| 1586682 | 1/1970 | France | 424/319 |
| 8205M | 9/1970 | France | 424/319 |
| 2258869 | 8/1975 | France | 424/319 |
| 857243 | 12/1960 | United Kingdom | 424/319 |
| 1364971 | 8/1974 | United Kingdom | 424/319 |

*Primary Examiner*—Bernard Helfin
*Assistant Examiner*—Vera C. Clarke
*Attorney, Agent, or Firm*—Sherman & Shalloway

[57] ABSTRACT

Compositions comprising mixtures of certain amino acids and vitamins particularly useful in the formulation of topically-applicable cosmetic compositions. The topical application of the compositions acts to improve the general complexion of the skin and to invigorate and revitalize the hair and scalp. Separate formulations are provided for each use.

20 Claims, No Drawings

AMINO ACID-VITAMIN FORMULATIONS FOR SKIN, HAIR AND SCALP CONDITIONERS

BACKGROUND OF THE INVENTION

1. Field of the Invention

The present invention relates to compositions comprising mixtures of certain amino acids and vitamins useful in cosmetic formulations for topical application to the skin, hair and scalp.

2. Description of the Prior Art

A variety of compositions containing amino acids and vitamins have long been known to be used with a host of dietary formulations either as nutritional supplements or in conjunction with other medicaments to correct specific physiological dysfunctions. All of the prior art patents reviewed containing amino acid-vitamin components generally involve the oral ingestion or the intravenous injection by the subject of the amino acid-vitamin combination formulation. For example, U.S. Pat. No. 3,914,419 discloses stable aqueous multivitamin preparations containing amino acids for intramuscular injection. U.S. Pat. No. 3,962,416 discloses an encapsulated nutrient comprising vitamins, amino acids, lipids, enzymes and minerals. U.S. Pat. No. 3,697,287 relates to an amino acid food composition comprising all the essential amino acids and vitamins. U.S. Pat. No. 2,887,437 discloses a distingerable and palatable tablet comprising specific vitamins and amino acids. U.S. Pat. No. 3,256,095 discloses a complete synthetic diet comprising an amino acid-vitamin composition. U.S. Pat. No. 3,773,930 also relates to a dietary composition having the subject combination. U.S. Pat. No. 3,639,587 provides amino acid-vitamin compositions as components for medicinal compositions for animals.

The prior art also discloses the use of amino acids alone as components in hair or scalp conditioning compositions. In this regard, U.S. Pat. No. 3,778,502 discloses a method of combatting scaling of scalp by applying to the scalp a solution of specific amino acids together with other organic acids. U.S. Pat. No. 3,849,576 relates to compositions comprising as an active ingredient, a derivative of cysteine or cysteamine, which is useful for the treatment of skin and scalp. U.S. Pat. No. 3,997,659 relates to hair bleaching compositions containing arginine or various proteins or polypeptides having a high arginine content. U.S. Pat. No. 3,998,761 relates to a shampoo composition containing as an essential conditioning ingredient a relatively high level of beer solids which, of course, contain a mixture of amino acids.

However, none of the prior art references disclose the specific combination of amino acids and vitamins for topical application according to the present invention which unobviously improves the general appearance of the skin, hair and scalp.

SUMMARY OF THE INVENTION

It has been discovered that mixtures of certain amino acids and vitamins within narrow concentrations provide compositions which are useful for topical application to the skin, hair and scalp to enhance softness and luster to the hair and to improve the general appearance of the skin. Separate formulations are provided for the skin and for the hair and scalp. Thus, the hair and scalp conditioner active compositions of this invention comprise mixtures of amino acids and vitamins in the following proportions given in grams per liter of the active composition:

|  | Minimum | Maximum |
| --- | --- | --- |
| Vitamin $B_6$ | 1.80 grams | 12.00 grams |
| Vitamin $B_5$ | 1.80 | 15.00 |
| Vitamin $B_3$ | 1.20 | 7.50 |
| Methionine | 0.75 | 4.00 |
| Arginine | 0.54 | 5.00 |
| Cysteine | 0.70 | 3.00 |
| Cysteine hydrochloride | 0.90 | 3.20 |
| Phenylalanine | 0.45 | 2.50 |
| Leucine | 0.30 | 2.25 |
| Lysine | 0.20 | 3.00 |
| Glycine | 0.28 | 2.50 |
| Valine | 0.10 | 2.00 |
| Iso-leucine | 0.12 | 2.00 |
| Tryptophane | 0.06 | 1.20 |
| Histidine | 0.05 | 0.50 |
| Tyrosine | 0.03 | 0.20 |
| Threonine | 0.40 | 3.40 |
| Zinc sulfate | 2.50 | 3.00 |
| Cystine | 0.003 | 0.02 |
| Propylene glycol | 250.0 ml | 700.0 ml |
| Vitamin D | 100,000.0 I.U. | 200,000.0 I.U. |
| Vitamin A | 34,000.0 I.U. | 170,000.0 I.U. |
| Vitamin E | 13,040.0 I.U. | 43,000.0 I.U. |

Compositions useful for the treatment of the skin according to this invention comprise mixtures of amino acids and vitamins in the following proportions given in grams per liter of the active composition:

|  | Minimum | Maximum |
| --- | --- | --- |
| Vitamin $B_5$ | 2.90 grams | 9.00 grams |
| Vitamin $B_6$ | 1.60 | 6.00 |
| Vitamin $B_3$ | 0.90 | 5.00 |
| Arginine | 0.86 | 6.00 |
| Cysteine | 0.40 | 2.00 |
| Lysine | 0.89 | 2.50 |
| Tryptophane | 0.19 | 1.00 |
| Histidine | 0.10 | 0.50 |
| Tyrosine | 0.10 | 0.20 |
| Cystine | 0.003 | 0.02 |
| Vitamin D | 100,000.0 I.U. | 200,000.0 I.U. |
| Vitamin A | 34,000.0 I.U. | 170,000.0 I.U. |
| Vitamin E | 35,050.0 I.U. | 73,000.0 I.U. |

The invention includes a method for preparing the novel amino acid-vitamin compositions for hair and scalp conditioners, which comprises a series of manipulative steps to produce stable homogeneous products. These steps include:

(a) preparation of cystine diluent;
(b) preparation of an amino acid mixture;
(c) preparation of a vitamin mixture using the cystine diluent of step (a);
(d) blending the amino acid mixture of step (b) with the vitamin mixture of step (c);
(e) incorporating additional vitamin components into the mixture of step (d);
(f) adding an aqueous solution of zinc sulfate into the amino acid-vitamin mixture of step (e); and
(g) incorporating adjuvants into the mixture of step (f);

and thus forming a stable homogeneous composition.

In addition, this invention encompasses a process for treating the skin and the hair and scalp comprising contacting the skin and the hair and scalp with the respective compositions described above.

Accordingly, it is an object of this invention to provide novel compositions for use in topical cosmetic formulations.

Another object of this invention is to prepare novel compositions which may be incorporated in cosmetic formulations.

A still further object of this invention is to provide a method for the treatment of hair and scalp to condition the hair and revitalize the scalp.

These and other objects are obtained by the present invention, as will become apparent from the following specification and claims.

DESCRIPTION OF THE PREFERRED EMBODIMENTS

In accordance with this invention, it has been found that certain amino acids in combination with certain vitamins provide novel compositions which have unusual cosmetic and conditioning properties, while another specific combination of amino acids and vitamins impart unusual cosmetic and conditioning properties to the skin.

Of equal importance is the novel procedure by which these compositions are produced.

The initial step in the process of preparing the hair and scalp active compounds consists of the preparation of a cystine diluent. This involves introducing cystine into a vessel and refluxing until all the cystine dissolves. In another vessel, a mixture of amino acids is dissolved in distilled water and the mixture is heated to boiling, then is refluxed until all the contents dissolve, and then cooled. In yet another vessel, a portion of the cystine diluent made in the first step and the vitamin mixture component are mixed until an emulsion is formed. To this vitamin emulsion is added sequentially the amino acid solution prepared in a separate vessel, a polyhydric alcohol solvent, vitamin D (ergocalciferol in a solution of a lower alkanol), vitamin E (d-$\alpha$-tocopherol) in an oil and a conventional surfactant. The additional vitamin E (d-$\alpha$-tocopherol polyethylene glycol 1000 succinate) is added to the resulting solution and thoroughly mixed with zinc sulfate to provide a blend of active compounds.

In the preparation of the skin conditioner active compositions, the cystine diluent, amino acid solution and the vitamin mixture are prepared in the same manner described above, albeit the amino acid combination, and the concentration of amino acid and vitamin mixtures are different. Only, arginine, cysteine, lysine, tryptophane, histidine and tyrosine are the amino acids used in this system. The procedure also differs in that polyhydric alcohol is first added to the amino acid solution and then followed by sequentially adding, a vitamin D solution, the vitamin mixture, a cosmetic base, vitamin E and additional vitamin E in the form of d-$\alpha$-tocopherol polyethylene glycol 1000 succinate.

It should be understood that other methods of mixing can be used and the order of the manipulative steps can vary without interfering with the efficacy of the active compound, although the stability of the final composition may be less than that desired.

The amino acids employed in this invention encompass the $\alpha$-amino acids which include neutral $\alpha$-amino acids, i.e., those having an equal number of amino groups and carboxyl groups, basic $\alpha$-amino acids, i.e., those having more basic groups than carboxyl groups, and acidic $\alpha$-amino acids, i.e., those having more carboxyl groups than amino groups. Natural and/or synthetic $\alpha$-amino acids are intended, including those termed essential and nonessential amino acids.

Examples of essential $\alpha$-amino acids or derivatives thereof are 1-arginine, which is 1-amino-4-guanidovaleric acid; 1-arginine hydrochloride, which is $C_6H_{14}N_4O_2C_6H_3N_3O_7 2H_2O$; 1-histidine, which is $\alpha$-amino-4-imidazolepropionic acid; dl-histidine; 1-histidine dihydrochloride; 1-isoleucine, which is $\alpha$-amino-$\beta$-methylvaleric acid; dl-isoleucine; 1-alloisoleucine; 1-leucine, which is $\alpha$-aminoisocaproic acid; dl-leucine; 1-lysine, which is $\alpha\epsilon$-diaminocaproic acid; 1-lysine monopicrate, which is $C_6H_{14}N_2O_2C_6H_3N_3O_7$; 1-lysine dihydrochloride, which is $C_6H_{14}N_2O_2.2HCl$; 1-lysine monohydrochloride, which is $C_6H_{14}N_2O_2.HCl$; dl-lysine dihydrochloride; dl-lysine monohydrochloride; dl-monopicrate; 1-methionine, which is $\gamma$-amino-$\alpha$-methylmercaptobutyric acid; dl-methionine; 1-phenylalanine, which is $C_6H_5CH(NH_2)CO_2H$; dl-phenylalanine; 1-phenylalanine picrolonate, which is $C_9H_{11}NO_2.C_{10}H_8N_4O_5$; dl-phenylalanine picrate, which is $(C_9H_{11}NO_2C_6H_3N_3O_7$; 1-threonine, which is $\alpha$-amino-$\beta$-hydroxybutyric acid; the monobenzoyl derivative of 1-threonine, which is $C_{11}H_{13}NO_4$; 1-threonine picrate, which is $C_{10}H_{12}N_4O_{10}$; dl-threonine hemihydrate; dl-threonine; 1-tryptophane, which is 1-$\alpha$-amino-3-indolepropionic acid; 1-tryptophane hydrochloride, which is $C_{11}H_{12}N_2O_2$. HlC; 1-tryptophane picrate, which is $C_{11}H_{11}N_2O_2.C_6H_6N_3O_7$; dl-tryptophane; 1-valine, which is $\alpha$-aminoisovaleric acid; and dl-valine.

Other $\alpha$-amino acids and derivatives thereof which can be added, for example, are the following neutral $\alpha$-amino acids and derivatives thereof: glycine, which is aminoacetic acid, $CH_2(NH_2)COOH$; glycine hydrochloride; tyrosine, which is $\alpha$-amino-$\beta$-(4-hydroxyphenyl) propionic acid; cysteine, which is $\alpha$-amino-$\beta$-mercaptopropionic acid, $HSCH_2CH(NH_2)COOH$; cysteine hydrochloride, cystine which is 3,3'-dithiobis(2-aminopropanoic acid); and cystine hydrochloride. The amino acids can be used in either their levorotary (l) or racemic (dl) forms.

The vitamins employed in this invention are a specific mixture of Vitamin A, Vitamin $B_3$, Vitamin $B_5$, Vitamin $B_6$, Vitamin D and Vitamin E. The vitamins are incorporated into the formulations in any suitable form. Examples of vitamins which are added are listed below: Vitamin A is 3,7-dimethyl-9-(2,6,6-trimethyl-1-cyclohexen-1-yl)-2,4,6-nonatetraen-1-ol and can be produced by total synthesis. The esters of Vitamin A are more stable to oxidation. Vitamin A acetate is $C_{22}H_{22}O_2$, and can be extracted from fish liver oils. Neovitamin A is 5-cis-Vitamin A and is naturally occurring isomer of vitamin A. Vitamin $B_3$ is nicotinic acid amide or niacinamide. Vitamin $B_5$ is pantothenic acid or can be in the salt form of calcium-d-pantothenate. Vitamin $B_6$ is pyridoxine. Vitamin $B_6$ hydrochloride is also termed pyridoxine hydrochloride and is 5-hydroxy-6-methyl-3,4-pyridine dimethanol hydrochloride, which is an advantageous form of Vitamin $B_6$ which may be used in the practice of this invention. Vitamin D is 9,10-secoergosta-5,7,10(19), 22-tetraen-3$\beta$-ol or ergocalciferol. Vitamin E refers to $\alpha$-tocopherol and $\alpha$-tocopherol derivatives, such as $\alpha$-tocopherol esters including $\alpha$-tocopheryl acetate, $\alpha$-tocopheryl orotate and preferably, $\alpha$-tocopherol polyoxyalkylene glycol moiety, generally referred to as the polyethylene glycol moiety of the ester, has a molecular weight in a range from about 600 to about 6000, and preferably, from about 600 to about 1500. An example of such an ester and one which has been found to be particularly effective is α-tocopheryl polyoxyethylene glycol (1000) succinate wherein the polyoxyethylene glycol moiety of the molecule has an average molecular weight of about 1000.

The blends of the active compositions of this invention used for treating skin and hair and scalp have a pH range from about 4 to 8, and preferably, from about 4 to 6.

Suitable surface active agents may be incorporated into the active composition and may be nonionic or cationic in nature. Suitable anionic surfactants which are co-soluble with the water-alcohol solvent medium include the alkali metal salts of sulfated fatty alcohols or mixtures thereof having about 8 to 18 carbon atoms, e.g., sodium and potassium salts of sulfated cetyl alcohol, sodium and potassium salts of sulfated stearyl alcohol, sodium and potassium salts of sulfated lauryl alcohol, sodium and potassium salts of sulfated coconut fatty alcohols, and the like; alkali metal salts of alkyl esters of sulfated succinic acid having about 8 to 18 carbon atoms in the alkyl group such as the sodium salt of the dioctyl ester of sulfated succinic acid; alkali metal salts of sulfated fatty acid amides having 8 to 18 carbon atoms, e.g., sodium and potassium salts of sulfated lauric amide, sodium and potassium salts of sulfated stearic amide, sodium and potassium salts of sulfated oleic amide, sodium and potassium salts of ricinoleic amide, and the like.

Suitable compatible nonionic surfactants include alkylamine oxides having about 8 to 18 carbon atoms, such as myristyldimethylamine oxide, cetyldimethylamine oxide, lauryldimethylamine oxide, stearyldimethylamine oxide, and the like; fatty acid mono- and di-alkanolamides having about 8 to 18 carbon atoms such as lauric monoethanolamide, myristic monoethanolamide, stearic monoethanolamide, lauric diethanolamide, stearic diethanolamide, mixtures of coconut fatty acid mono- and di-ethanolamide. Further, suitable nonionic surfactants include polyethylene oxide condensates of castor oil. Other suitable nonionic surfactants include condensates of fatty acids, fatty alcohols, and fatty hydroxy acids, which are characteristic of lanolin or wool-fat, with 50 to 70 moles ethylene oxide. Such ethylene oxide condensates are available as water-soluble lanolin designated as ethoxylated lanolin. Acetylated derivatives of these ethoxylated lanolins may also be used as water-alcohol soluble nonionic surfactants. Additional suitable nonionic surfactants include condensates of higher fatty acids having about 8 to 18 carbon atoms, such as ricinoleic acid, with 3 moles ethylene oxide and condensates of the higher fatty alcohols having about 8 to 18 carbon atoms, exemplified by isooctyl alcohol, nonyl alcohol, decyl alcohol, and oleyl alcohol, with 3 moles ethylene oxide.

Suitable cationic surfactants include the quaternary ammonium compounds of mono- and di-alkylamines having from 8 to 18 carbons in the alkyl chain such as hexyltrimethyl ammonium chloride, dihexyldimethyl ammonium chloride, octyltrimethyl ammonium chloride, dioctyldimethyl ammonium chloride, 25 distearyldimethyl ammonium chloride, dicoco dimethyl ammonium chloride, and the like.

Preferred surfactants for use in this invention are non-ionic surface active agents which are polyoxyalkylene derivatives of hexitol anhydride partial fatty acid esters (e.g. TWEEN ® manufactured by I.C.I. United States, Wilmington, Delaware. Particularly preferred is a polyoxyalkylene derivative of sorbitan monooleate TWEEN ® 80).

The surfactant component is well known in the surfactant art and are employed in effective amounts, i.e., in an amount which is sufficient to provide a stable composition having skin, hair and scalp conditioning properties. In general from from about 0.05 to about 5 weight percent and preferably from about 0.5 to about 2 weight percent of a suitable surfactant or mixture of surfactants, based on the total weight of the final compositions, has been found satisfactory. Excessive amounts of surfactant tend to produce foams which are sticky and tacky to the touch, while insufficient amounts of surfactants provide a product having insufficient surface activity and skin, hair and scalp conditioning power.

The solvent system employed in the present invention comprises water and a mixture of monohydric and polyhydric alcohols. Any lower alkanol having one to 3 carbon atoms, e.g., methanol, ethanol, n-propanol and isopropanol can be employed. Polyhydric alcohols include lower alkylene glycols such as ethylene glycol, propylene glycol and glycerine.

The active compositions of this invention can also contain other known adjuvants, including for instance, bactericidal and bacteriostatic agents, detergents, penetrating agents, dyes, perfumes and the like. The carrier or excipient employed with the active compositions will depend on the form of the product desired. Additional ingredients, such as water, mineral oil, lanolin, lanolin derivatives, waxes, gelling agents, and suitable solvents can be compounded with the compositions of this invention to provide the desired form. It is well within the purview of those skilled in the cosmetic and pharmaceutical art to formulate stable lotions, creams, gels or aerosols containing the novel compositions. Thus, the active compounds can be applied topically to the skin and the hair and scalp as an aqueous dispersion, as a cream, as a gel, as a shampoo or an aerosol.

The blends of final formulations used for treating skin, hair and scalp have a pH range of from about 3 to 9 and preferably, about 4 to 6. This pH range is controlled by use of buffering agents well known to the art. In general, the buffering agents are prepared by using a solution of acids and salts, or alkali and salts. Examples of buffering solutions comprising weak acids and salts would be boric acid and sodium borate, citric acid and sodium citrate, citric acid and sodium biphosphate. Exemplary, of buffering solutions with either strong acids or bases and salts would be for example, potassium acid phthalate and hydrochloric acid mixtures and potassium acid phthalate and sodium hydroxide mixtures.

The term "topical" as employed in this application relates to the introduction of the cosmetic, incorporated in a suitable base or vehicle at the site of the area for the exertion of local action. Accordingly, such topical compositions include those forms in which the cosmetic formulation is applied externally by direct contact with the surface to be treated. Conventional forms for this purpose include ointments, lotions, pastes, jellies, powders, and the like. The term "ointments" embraces formulations (including creams) having oleogenous absorption, water-soluble and emulsion-type bases as described in *Reminton's Practice of Pharmacy*, 11th Edition (1956) page 336, Mack Publishing Company. Topical compositions as herein defined include also those forms which afford local as opposed to systemic release into the immediate affected areas where such areas are not accessible for direct external application, such forms being sprays, aerosols, drops, powders, sterile aqueous suspensions and the like.

In accordance with the present invention, the novel active compositions in a suitable carrier may be topically applied to the hair and scalp of the subject to improve overall conditions of the hair and scalp. The blend of active compounds for hair and scalp is present in amounts of 1 to 25 weight percent of the final formulation and preferably about 5 to 15 weight percent. As an added benefit, topical application to the hair imparts softness, fuller body and luster characteristics to the hair. Additionally, the hair remains natural in appearance and in feel and retains these properties over a long period.

In accordance with the present invention, a method for the treatment of hair and scalp conditioning involves the steps of applying sufficient heat, either wet or dry, by conventional means, to the scalp of the person to be treated until the pores are opened; topically applying to the scalp about 2 to 50 cc and preferably 2 to 10 cc of the above-described composition, depending on the area to be covered; further applying sufficient heat to the composition until the composition is absorbed by the scalp. This treatment is continued daily for approximately sixty days; thereafter, if desirable, the frequency of the treatment can be reduced to once a day for five days per week until the symptoms subside and then can be replaced by the application of a hair lotion containing said composition to the hair and scalp, or even by shampooing the scalp weekly with a detergent-containing solution of said composition. The beneficial effects produced by the practice of the present invention essentially can be observed by a healthier and cleaner scalp, the softness of the hair is enhanced and the general appearance thereof is improved.

In accordance with the present invention, it has been found that other specific novel amino acid-vitamin compositions are useful for the treatment of human skin. The skin conditioner may be applied in any convenient form described above. The compositions of this invention impart a smoothness and lubricity to the skin and enhance its complexion. Suitable concentrations of the active compositions for skin treatment can range from 5 weight percent to 25 weight percent of the final formulation, and preferably from 5 to 15 weight percent.

The following examples illustrate the present invention:

EXAMPLE I

Preparation of a hair and scalp conditioner.

The following process steps were employed:
(a) A cystine diluent is prepared by introducing 0.09 g of cystine into a screw-top flask containing 1 liter of distilled water, the contents are heated to boiling and refluxed until the cystine dissolves completely. The solution is cooled to room temperature.
(b) An amino acid mixture is prepared in another screw-top flask containing 250 ml of distilled water; the following mixture of amino acids was introduced:

| | |
|---|---|
| l-tyrosine | 0.10 grams |
| dl-histidine | 0.30 |
| l-tryptophane | 0.30 |
| l-iso-leucine | 0.53 |

-continued

| | |
|---|---|
| l-valine | 0.53 |
| glycine | 1.00 |
| l-lysine monohydrochloride | 1.00 |
| l-leucine | 1.58 |
| l-phenylalanine | 1.88 |
| l-cysteine | 2.10 |
| l-cysteine hydrochloride | 2.10 |
| l-arginine | 2.10 |
| dl-methionine | 3.25 |
| dl-threonine | 2.10 |

This mixture is boiled with constant agitation. Reflux conditions are maintained until all the amino acids are dissolved. Then the heating is discontinued and the solution cooled and maintained at 30° C.

(c) A vitamin mixture is prepared in yet another flask containing 125 ml of the cystine diluent made above by introducing the folllowing:

| | |
|---|---|
| pyridoxine hydrochloride | 6.25 grams |
| calcium-d-pantothenate | 5.25 |
| niacinamide | 5.25 |
| Vitamin A palmitate | 0.52 |

The mixture is stirred until all the ingredients are dispersed and the mixture is homogeneous.

(d) In a separate glass flask, a solution of ergocalciferol (Vitamin D) is prepared by dissolving 0.02 grams with 10 ml ethanol or isopropanol.

(e) A solution containing 250 l ml of the amino acid mixture and 125 ml of the vitamin mixture is prepared. To this solution is added with stirring 650 ml of propylene glycol U.S.P. followed by the addition of 2.5 ml of the ergocalciferol solution prepared in step (d). Next, 12.5 ml of Tween 80 and 33,400 I.U. of d-α-tocopherol in vegetable oil are introduced and thoroughly agitated until the resulting solution is homogeneous.

(f) An addition of 2,600 I.U. of D-α-tocopherol polyethylene glycol 1000 succinate in the liquid phase is added to the homogeneous solution prepared in step (e).

(g) To the resulting composition in step (f), an aqueous solution prepared by dissolving 2.5 grams of zinc sulfate (ZnSO$_4$.7H$_2$O) in 50 ml of distilled water is added with mixing. An effective amount of a suitable fragrance is added to provide a milky white lotion as a final product.

Tween 80 is a polyoxalkylene derivative of sorbitan monooleate, manufactured by the ICI United States, Inc., Wilmington, Del.

EXAMPLE II

Preparation of a skin lotion.

The following process steps are employed:
(a) A cystine diluent is prepared by introducing 0.09 g of l-cystine into 1 liter of distilled water, the contents are heated to boiling and refluxed until complete dissolution of the cystine occurs.
(b) In 328 ml of distilled water combine the following:

| | |
|---|---|
| l-arginine | 1.48 grams |
| l-cysteine | 0.82 |
| l-lysine monohydrochloride | 0.82 |

-continued

|  |  |
|---|---|
| l-tryptophane | 0.32 |
| dl-histidine | 0.16 |
| l-tyrosine | 0.13 |

Mix well and heat to boiling. Reflux until all the amino acids are dissolved. The refluxing should be accomplished with a minimum loss of water. Remove from reflux and cool to about 30° C.

(c) Into 82 ml of the cystine diluent prepared in step (a), the following were introduced:

|  |  |
|---|---|
| calcium-d-pantothenate | 4.92 grams |
| pyridoxine hydrochloride | 2.80 |
| niacinamide | 1.64 |
| Vitamin A palmitate | 0.55 |

The mixture is stirred constantly until the blend is emulsified.

The Vitamin A palmitate disperses evenly, but will not dissolve.

(d) In a separate flask, a solution is prepared by dissolving 0.02 gram of ergocalciferol (40,000,000 I.U. units/gram) in 10 ml of ethanol or isopropanol.

(e) To the aqueous amino acid solution prepared in step (b), 295 ml of propylene glycol and 246 ml of glycerol are added with constant stirring.

(f) To the solution prepared in step (e) is added with stirring 1.6 ml (131,200 I.U. units) of the ergocalciferol solution from step (d).

(g) With constant agitation, the vitamin blend of step (c) is added to the amino acid solution prepared in step (f).

(h) To the composition prepared in step (g), 59,000 I.U. of d-α-tocopherol (in oil) is added with constant stirring.

(i) To this liquid composition prepared in step (g), 2,600 I.U. of d-α-tocopherol polyethylene glycol 1000 succinate is added.

(j) An effective amount of a suitable fragrance is added to the composition of step (i) before it solidifies.

(k) The resulting mixture prepared in step (j) is added with stirring to 187 grams of a greaseless ointment base comprising sodium lauryl sulfate, cetyl alcohol, propylene glycol and a paraffin wax; stirring is continued until a homogeneous emulsion is obtained.

It should be understood that the various changes may be made in our process as herein described without affecting the improved results attained. Thus, the various modifications in conditions as to time, temperature, etc., and various changes in procedure differing from those herein given as illustrative of the preferred embodiments of our invention may be made without departure from the scope thereof. Accordingly, the scope of our invention is to be determined in accordance with the prior art and appended claims.

What is claimed is:

1. A composition for topical application to hair and scalp to enhance softness and luster and impart fuller body to the hair comprising a mixture of amino acids and vitamins in the following proportions given in grams per liter of the final composition:

|  | Minimum | Maximum |
|---|---|---|
| Vitamin $B_6$ | 1.80 grams | 12.00 grams |
| Vitamin $B_5$ | 1.80 | 15.00 |
| Vitamin $B_3$ | 1.20 | 7.50 |
| Methionine | 0.75 | 4.00 |
| Arginine | 0.54 | 5.00 |
| Cysteine | 1.60 | 6.20 |
| Phenylalanine | 0.45 | 2.50 |
| Leucine | 0.30 | 2.25 |
| Lysine | 0.20 | 3.00 |
| Glycine | 0.28 | 2.50 |
| Valine | 0.10 | 2.00 |
| Iso-leucine | 0.12 | 2.00 |
| Tryptophane | 0.06 | 1.20 |
| Histidine | 0.05 | 0.50 |
| Tyrosine | 0.03 | 0.20 |
| Threonine | 0.40 | 3.40 |
| Zinc sulfate | 2.50 | 3.00 |
| Vitamin D | 100,000.0 I.U. | 200,000.0 I.U. |
| Vitamin A | 34,000.0 I.U. | 170,000.0 I.U. |
| Vitamin E | 13,050.0 I.U. | 43,000.0 I.U. |
| in an excipient. |  |  |

2. The composition according to claim 1, additionally containing at least one monohydric and at least one polyhydric alcohol.

3. The composition according to claim 2, wherein the said alcohol is selected from the group consisting of lower alkanols, alkylene glycols and glycerols.

4. The composition according to claim 1, additionally containing a cationic or nonionic surfactant.

5. The composition according to claim 4, wherein the surfactant is a polyoxyalkylene derivative of sorbitan monooleate.

6. The composition according to claim 1, wherein said composition is in the form of a stable emulsion.

7. The composition according to claim 1, wherein said excipient is a pharmaceutically acceptable base.

8. The composition according to claim 1 as a lotion.

9. The composition according to claim 1 as a cream.

10. A method of treating hair and scalp to enhance softness and luster and to impart fuller body to the hair comprising the step of topically applying to the hair and scalp, as an active composition, the mixture of amino acids and vitamins according to claim 1.

11. The method of treating hair and scalp according to claim 10, comprising the steps of applying sufficient heat to open the pores of the scalp, topically applying said composition to said hair and scalp, and drying the treated hair and scalp.

12. The method of claim 10, wherein the final composition contains from 1 to 25 weight percent of said active composition.

13. The method of claim 12, wherein the final composition contains from 5 to 15 weight percent of said active composition.

14. A composition for topical application to the skin to improve the general appearance thereof comprising a mixture of amino acids and vitamins in the following proportions given in grams per liter of the final composition:

|  | Minimum | Maximum |
|---|---|---|
| Vitamin $B_5$ | 2.90 grams | 9.00 grams |
| Vitamin $B_6$ | 1.60 | 6.00 |
| Vitamin $B_3$ | 0.90 | 5.00 |
| Arginine | 0.86 | 6.00 |
| Cysteine | 0.40 | 2.00 |
| Lysine | 0.89 | 2.50 |
| Tryptophane | 0.19 | 1.00 |
| Histidine | 0.10 | 0.50 |

-continued

|  | Minimum | Maximum |
|---|---|---|
| Tyrosine | 0.10 | 0.20 |
| Cystine | 0.003 | 0.02 |
| Vitamin D | 100,000.0 I.U. | 200,000.0 I.U. |
| Vitamin A | 34,000.0 I.U. | 170,000.0 I.U. |
| Vitamin E | 35,050.0 I.U. | 73,000.0 I.U. |
| in an excipient. | | |

15. The composition according to claim 14, wherein said excipient is a greaseless ointment base comprising sodium lauryl sulfate, cetyl alcohol, propylene glycol and a paraffin wax.

16. The method of treating skin to improve the general appearance thereof which comprises the step of topically applying to the skin area as an active composition the mixture of amino acids and vitamins according to claim 14.

17. The method of claim 16, wherein the final composition contains from 5 to 25 weight percent of said active composition.

18. The method of claim 17, wherein the final composition contains from 5 to 15 weight percent of the active composition.

19. A method for the preparation of a composition comprising a mixture of amino acids and vitamins for topical application to the hair and scalp which comprises the steps of:

(a) preparing a cystine diluent by combining cystine and water and heating until the cystine dissolves in the water;

(b) preparing an aqueous solution of the following amino acids: methionine, arginine, cysteine, phenylalanine, leucine, lysine, glycine, valine, iso-leucine, tryptophane, histidine, tyrosine and threonine;

(c) preparing a vitamin blend of vitamin A, vitamin $B_3$, vitamin $B_5$ and vitamin $B_6$ in the cystine diluent prepared in step (a);

(d) combining the aqueous amino acid solution of step (b) with the vitamin blend of step (c); and (e) incorporating vitamin D and vitamin E into the mixture of step (d);

(f) adding an aqueous solution of zinc sulfate into the amino acid-vitamin mixture of step (e);

(g) incorporating an excipient into the mixture of step (f) and thus forming a stable homogeneous composition;

wherein the amount of the active amino acids and vitamins in the final composition are in the following proportions given in terms of grams per liter:

| Active Ingredient | Minimum | Maximum |
|---|---|---|
| Vitamin $B_6$ | 1.80 grams | 12.00 grams |
| Vitamin $B_5$ | 1.80 | 15.00 |
| Vitamin $B_3$ | 1.20 | 7.50 |
| Methionine | 0.75 | 4.00 |
| Arginine | 0.54 | 5.00 |
| Cysteine | 1.60 | 6.20 |

-continued

| Active Ingredient | Minimum | Maximum |
|---|---|---|
| Phenylalanine | 0.45 | 2.50 |
| Leucine | 0.30 | 2.25 |
| Lysine | 0.20 | 3.00 |
| Glycine | 0.28 | 2.50 |
| Valine | 0.10 | 2.00 |
| Iso-leucine | 0.12 | 2.00 |
| Tryptophane | 0.06 | 1.20 |
| Histidine | 0.05 | 0.50 |
| Tyrosine | 0.03 | 0.20 |
| Cystine | 0.003 | 0.02 |
| Threonine | 0.40 | 3.40 |
| zinc sulfate | 2.50 | 3.00 |
| Vitamin D | 100,000.0 I.U. | 200,000.0 I.U. |
| Vitamin A | 34,000.0 I.U. | 170,000.0 I.U. |
| Vitamin E | 13,050.0 I.U. | 43,000.0 I.U. |

20. A method for the preparation of a composition comprising a mixture of amino acids and vitamins for topical application to the skin which comprises the steps of:

(a) preparing a cystine diluent by combining cystine and water and heating until the cystine dissolves in the water;

(b) preparing an aqueous solution of the following amino acids: arginine, cysteine, lysine, histidine and tyrosine;

(c) preparing a vitamin solution comprising vitamin A, vitamin $B_5$, vitamin $B_6$ and vitamin $B_3$ in the cystine diluent of step (a);

(d) separately preparing a vitamin D solution;

(e) adding to the aqueous amino acid solution prepared in step (b) at least one polyhydric alcohol;

(f) adding to the solution prepared in step (e) a portion of the vitamin D solution of step (d);

(g) combining the resulting amino acid solution of step (f) with the vitamin blend of step (c);

(h) adding vitamin E to the components of step (g) and mixing until the mixture becomes homogeneous;

(i) adding the composition of step (h) to an excipient with constant stirring until the composition becomes homogeneous and thus forming a stable composition;

wherein the amounts of the active ingredient amino acids and vitamins in the final composition are in the following proportions given in terms of grams per liter:

|  | Minimum | Maximum |
|---|---|---|
| Vitamin $B_5$ | 2.90 grams | 9.00 grams |
| Vitamin $B_6$ | 1.60 | 6.00 |
| Vitamin $B_3$ | 0.90 | 5.00 |
| Arginine | 0.86 | 6.00 |
| Cysteine | 0.40 | 2.00 |
| Lysine | 0.89 | 2.50 |
| Tryptophane | 0.19 | 1.00 |
| Histidine | 0.10 | 0.50 |
| Tyrosine | 0.10 | 0.20 |
| Cystine | 0.003 | 0.02 |
| Vitamin D | 100,000.0 I.U. | 200,000.0 I.U. |
| Vitamin A | 34,000.0 I.U. | 170,000.0 I.U. |
| Vitamin E | 35,050.0 I.U. | 73,000.0 I.U. |

* * * * *